US00PP18185P2

(12) United States Plant Patent
Van Zanten

(10) Patent No.: US PP18,185 P2
(45) Date of Patent: Nov. 6, 2007

(54) ***OSTEOSPERMUM* PLANT NAMED 'GG DEL WC06'**

(50) Latin Name: *Osteospermum ecklonis*
Varietal Denomination: GG DEL WC06

(75) Inventor: Leo Van Zanten, Oxnard, CA (US)

(73) Assignee: Grolink Corporation, Oxnard, CA (US)

( * ) Notice: Subject to any disclaimer, the term of this patent is extended or adjusted under 35 U.S.C. 154(b) by 0 days.

(21) Appl. No.: 11/394,706

(22) Filed: Mar. 31, 2006

(51) Int. Cl.
*A01H 5/00* (2006.01)

(52) U.S. Cl. ..... Plt./360
(58) Field of Classification Search ..... Plt./360
See application file for complete search history.

*Primary Examiner*—Wendy C. Haas
*Assistant Examiner*—Georgia Helmer

(57) ABSTRACT

A new and distinct *Osteospermum* plant cultivar is disclosed, characterized by large daisy type inflorescences, freely flowering under outdoor growing conditions with continuous blooming from spring through autumn, bright white ray florets, multiple stripes of violet, blue and purple on under surface of ray florets and dark blue disc florets.

1 Drawing Sheet

Latin name of the genus and species: *Osteospermum ecklonis.*
Variety denomination: 'GG DEL WC06'.

BACKGROUND OF THE INVENTION

The new cultivar 'GG DEL WC06' is a product of open pollination in a heterogeneous population of *Osteospermum* mass selection. The new cultivar was discovered and selected by Leo Van Zanten in May 2004 in Carpinteria, Calif.

Asexual reproduction of the new cultivar 'GG DEL WC06' by cuttings from adventitious shoots was performed in Oxnard, Calif., and has shown that the unique features of this new cultivar are stable and reproduced true to type on successive generations.

SUMMARY OF THE INVENTION

The cultivar 'GG DEL WC06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG DEL WC06.' These characteristics in combination distinguish 'GG DEL WC06' as a new and distinct *Osteospermum* cultivar:

1. Large daisy type inflorescence;
2. Very bright white ray florets;
3. Dark blue disc florets;
4. Multiple stripes of violet, blue and purple on under surface of ray florets; and
5. A free branching habit.

There is no parent variety to compare to 'GG DEL WC06'.

In comparison to the commercially available variety 'Cape Daisy Nairobi' (U.S. Plant Pat. No. 10,340), 'GG DEL WC06' is shorter but wider than the comparable variety. Also, the leaves of 'GG DEL WC06' are much smaller and a different shape. Additionally, there are more disc florets, making a wider disc diameter than the comparable variety. Further, the ray florets are longer and wider, though the inflorescence diameter of 'GG DEL WC06' is smaller than that of 'Cape Daisy Nairobi.' Finally, the under surface of the ray florets of the new variety are much darker and have a wider range of violet-blue colors compared to the very light purple under surface of the ray florets of the comparable variety.

BRIEF DESCRIPTION OF THE PHOTOGRAPH

The accompanying photograph in FIG. 1 illustrates in full color a typical plant of 'GG DEL WC06' grown in a 6-inch pot, planted late October and grown outdoors. The plant is 18 weeks old. The growing temperature ranged from 12° C. to 15° C. at night to 12° C. to 20° C. during the day. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG DEL WC06' plants grown in Oxnard, Ventura County, Calif., during the months of October through February. The growing temperature ranged from 12° C. to 15° C. at night to 12° C. to 20° C. during the day. Measurements and numerical values represent averages of typical flowering types.

Botanical classification: *Osteospermum ecklonis* cultivar 'GG DEL WC06.'
Commercial classification: Garden-type *Osteospermum.*

PROPAGATION

Time to rooting: 10 to 14 days at approximately 21° C.
Root description: Fine, fibrous.

PLANT

Growth habit: Mounding outwardly spreading herbaceous perennial.
Height: Approximately 21 cm.
Plant spread: Approximately 53 cm.
Growth rate: Vigorous.
Branching characteristics: Free Branching.
Length of lateral branches: Approximately 8 cm.
Number of leaves per lateral branch: Approximately 62.
Age of plant described: Approximately 130 days.

FOLIAGE

Leaf:
*Arrangement.*—Alternate single.
*Average length.*—Approximately 3.6 cm.
*Average width.*—Approximately 2.2 cm.
*Shape of blade.*—Obovate.
*Apex.*—Abruptly acuminate.
*Base.*—Attenuate.
*Attachment.*—Stalked.
*Margin.*—Entire with occasional tiny serrations.
*Texture of top surface.*—Lightly pubescent.
*Texture of bottom surface.*—Lightly pubescent.
*Leaf internode length.*—Approximately 1 cm.
*Color.*—Young foliage upper side: Near Yellow-Green 147A. Young foliage under side: Near Green 137A. Mature foliage upper side: Near Yellow-Green 147A. Mature foliage under side: Near Green 137A.
*Venation.*—Type: Pinnate. Venation color upper side: Near Yellow-Green 144C. Venation color under side: Near Yellow-Green 144B.
Petiole:
*Average length.*—Approximately 1.7 cm.
*Color.*—Near Yellow-Green 144B.
*Diameter.*—Approximately 0.3 cm.

BLOOM

Inflorescence:
*Flowering habit.*—Freely flowering under outdoor growing conditions with continuous blooming from spring through autumn and year round in a greenhouse environment.
*Inflorescence form.*—Daisy.
*Natural flowering season.*—Continuous throughout February to September in temperature regions.
*Number of inflorescences per lateral branch.*—Approximately 6 open inflorescences.
*Inflorescence diameter.*—Approximately 6.2 cm.
*Inflorescence depth.*—Approximately 3 cm.
*Disc diameter.*—Approximately 1.5 cm.
*Inflorescence longevity on plant.*—Approximately 5 to 10 days, longevity of individual flowers are very dependent on temperature and light conditions.
*Persistence.*—Persistent.
Ray florets:
*Appearance.*—Matte.
*Texture.*—Smooth, velvety.
*Average number of ray florets per inflorescence.*—18.
*Shape.*—Oblanceolate.
*Aspect.*—Slightly cupped, facing upward or outward.
*Margin.*—Entire.
*Apex.*—Obtuse.
*Length.*—Approximately 4.2 cm.
*Width.*—Approximately 1.6 cm.
*Color.*—Upper surface at first opening: At base, two stripes of near Violet-Blue 90A; brighter than White 155D and near Violet-Blue 90A at extreme tip. Upper surface at maturity: At base, two stripes of near Violet-Blue 90A; brighter than White 155D and near Violet-Blue 90A at extreme tip. Upper surface at fading: At base, two stripes of near Violet-Blue 90A; brighter than White 155D and near Violet-Blue 90B at extreme tip. Under surface at first opening: Near Purple 76D with longitudinal stripes of near Violet-Blue 97B, stripes of near Violet 84B and stripes of near Blue 102C. Under surface at maturity: Near Purple 76D with longitudinal stripes of near Violet-Blue 97B, stripes of near Violet 84B and stripes of near Blue 102C. Under surface at fading: Near Purple 76D with longitudinal stripes of near Violet-Blue 97B, stripes of near Violet 84B and stripes of near Blue 102C.
Disc florets:
*Appearance.*—Shiny.
*Texture.*—Smooth.
*Average number of florets per disc.*—Approximately 72.
*Shape.*—Tubular.
*Apex.*—Five-pointed.
*Average length.*—Approximately 0.4 cm.
*Average width.*—Approximately 0.1 cm.
*Color.*—At first opening: Near Violet-Blue 93A. At maturity: Near Violet-Blue 93A. At fading: Near Violet-Blue 93A.
Peduncle:
*Length.*—Approximately 14.3 cm.
*Angle.*—Terminal peduncles, erect; secondary and tertiary peduncles, about 45° from vertical.
*Strength.*—Moderate.
*Color.*—Near Yellow-Green 146B with shades of Yellow-Green 148A.
*Habit.*—Upright.
*Diameter.*—Approximately 0.1 cm.
*Surface texture.*—Lightly pubescent.
Inflorescence bud:
*Length.*—Approximately 1.7 cm.
*Diameter.*—Approximately 1 cm.
*Form.*—Ovoid to elliptic.
*Color.*—Near Green 137A.
Involucral bracts (phyllaries):
*Appearance.*—Matte.
*Texture.*—Lightly pubescent.
*Number.*—Approximately 15.
*Shape.*—Lanceolate.
*Margin.*—Entire.
*Apex.*—Narrowly acute.
*Length.*—Approximately 1.3 cm.
*Width.*—Approximately 0.2 cm.
*Color.*—Upper side: Near Green 137A. Under side: Near Green 137A.

REPRODUCTIVE ORGANS

Androecium: Present on disc florets only.
*Number of stamens.*—5.
*Anther shape.*—Linear.
*Anther length.*—Approximately 1.4 mm.
*Anther color.*—Near Violet-Blue 93A.
*Amount of pollen.*—Not abundant.
*Pollen color.*—Near Yellow-Orange 21A.

Gynoecium: Present on ray and disc florets.

*Pistil number.*—One.

*Pistil length.*—Approximately 5 mm.

*Stigma shape.*—Two parted.

*Stigma length.*—Approximately 1.1 mm.

*Stigma color.*—Near Purple 79A.

*Style length.*—Approximately 0.1 cm.

*Style color.*—Near Purple 79A.

OTHER CHARACTERISTICS

Disease resistance: Neither resistance nor susceptibility to disease or pests has been observed in this variety.

Drought tolerance/cold tolerance: Plants are moderately drought tolerant. Plants need cold, less than 12.8° C. for flower induction.

Fruit/seed production: Commercially, this plant is not used or observed in a stage where seeds would be produced. Therefore, seed production has not been observed.

What is claimed is:

1. A new and distinct cultivar of *Osteospermum* plant named 'GG DEL WC06' as herein illustrated and described.

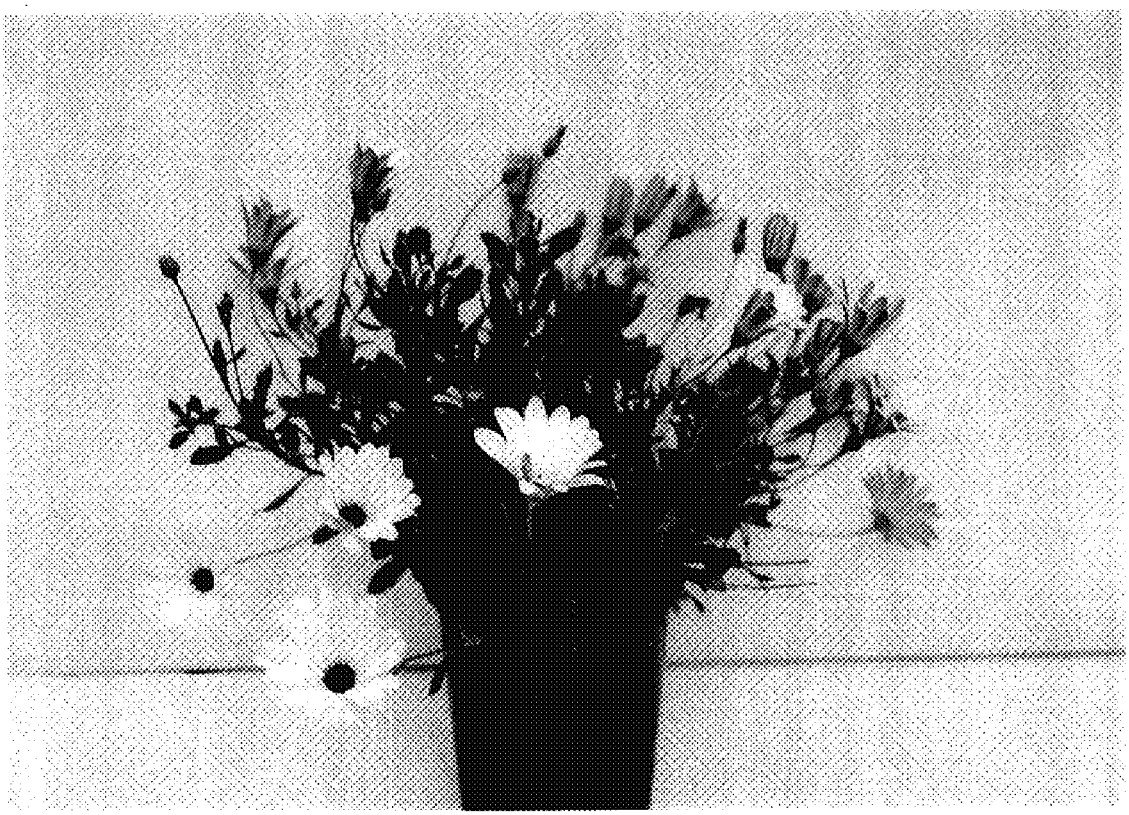

* * * * *